United States Patent [19]

Farleman et al.

[11] Patent Number: 4,634,273

[45] Date of Patent: Jan. 6, 1987

[54] O-RING INSPECTION METHOD

[75] Inventors: Ronald K. Farleman, Reminderville; Charles W. Fetheroff, Willowick; Istvan M. Matay, North Royalton, all of Ohio

[73] Assignee: TRW Inc., Cleveland, Ohio

[21] Appl. No.: 618,595

[22] Filed: Jun. 8, 1984

[51] Int. Cl.⁴ .................... G01N 21/88; G01B 11/08
[52] U.S. Cl. ..................................... 356/73; 356/237; 356/387
[58] Field of Search ................ 356/73, 384, 385, 386, 356/237, 387; 250/560, 562, 563

[56] References Cited

U.S. PATENT DOCUMENTS

| | | |
|---|---|---|
| 2,487,628 | 11/1949 | Aller . |
| 3,025,748 | 3/1962 | Schoepe et al. . |
| 3,619,065 | 11/1971 | Agnew . |
| 3,758,214 | 9/1973 | Mangelsdorf . |
| 3,778,167 | 12/1973 | Clanet et al. ................. 356/237 X |
| 3,782,827 | 1/1974 | Nisenson et al. . |
| 3,806,252 | 4/1974 | Harris et al. . |
| 3,918,816 | 11/1975 | Foster et al. . |
| 4,062,633 | 12/1977 | Stapleton et al. .................. 356/385 |
| 4,298,285 | 11/1981 | Ito . |
| 4,467,214 | 8/1984 | Ito et al. ......................... 356/237 X |

FOREIGN PATENT DOCUMENTS 1454757 11/1976 United Kingdom .............. 356/237

Primary Examiner—Davis L. Willis
Assistant Examiner—Matthew W. Koren
Attorney, Agent, or Firm—Yount & Tarolli

[57] ABSTRACT

A method is provided to inspect a resiliently deflectable O-ring which tends to distort under the influence of its own weight. The O-ring is placed on a transparent support member with the central axis of the O-ring in a vertical orientation. Light is directed toward the O-ring and through the support member to cause the O-ring to cast a shadow. The distance between portions of the shadow cast by diametrically spaced apart portions of the O-ring indicate diametral measurements of the O-ring. The distance between radial edge portions of the shadow cast by the O-ring indicates the thickness of the O-ring. To detect surface flaws in the O-ring, light is directed against a small area on the surface of the O-ring while it is rotated. A variation in the characteristics of the reflected light indicates the presence of a flaw in the surface of the O-ring. To provide for scanning of inner and outer surface areas of the O-ring to detect surface flaws, the O-ring may be rotated about an axis which extends perpendicular to the central axis of the O-ring and is tangential to a circle through the center of the cross section of the O-ring.

28 Claims, 13 Drawing Figures

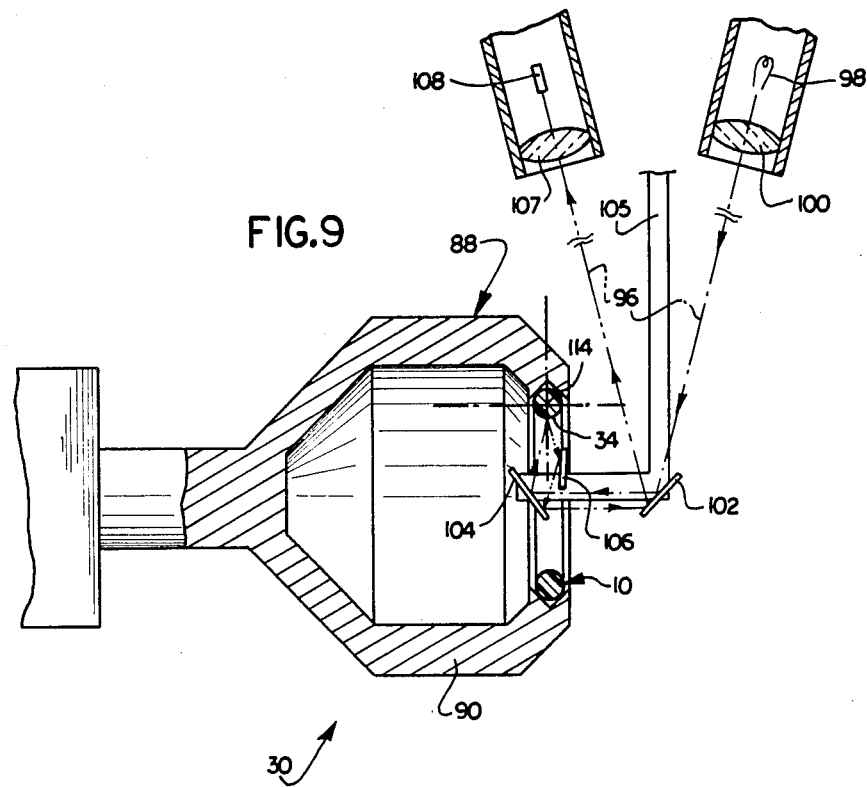
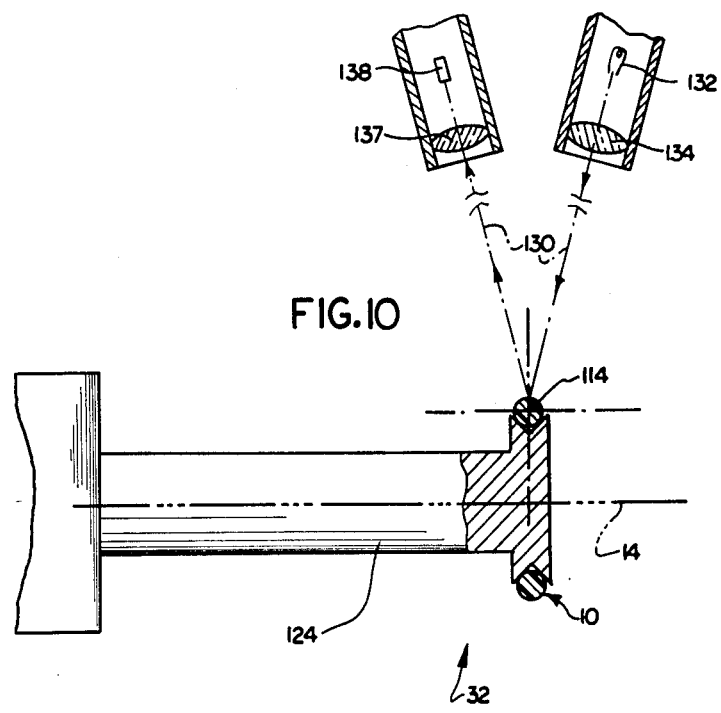

O-RING INSPECTION METHOD

BACKGROUND OF THE INVENTION

The present invention relates to a new and improved method for inspecting O-rings and more specifically to a method of determining the diameter, thickness and/or locating flaws in the surface of an O-ring.

Standard elastomeric O-rings are frequently used as cheap seals in non-critical areas subjected to relatively mild operating conditions. When standard elastomeric O-rings have been used as seals in critical areas subjected to severe operating conditions, problems have been encountered. For the most part, these problems are a result of the fact that O-rings are commonly manufactured at high production rates with a minimum of care in order to minimize the cost of the O-rings. As a result, in critical use areas, O-rings must be 100% inspected.

Inspection of O-rings is a labor-intensive, time-consuming and tedious process which is presently performed manually without the use of sophisticated gauges or automated equipment. Each O-ring is inspected to be certain that its inside diameter, outside diameter, and/or thickness is within specified tolerance ranges. The determination of the inside and/or outside diameter of an O-ring is difficult since the O-ring is readily deflected and tends to distort whenever it is engaged by a solid measuring device. When the O-ring is held in an upright orientation by engaging one radial segment of the O-ring, the O-ring tends to distort under the influence of its own weight.

In addition, O-rings are also inspected for numerous types of surface flaws. These surface flaws include backrind, blister, excessive trimming, flash, flow marks, foreign materials, mismatch, mold deposit indentations, non-fill, off-register, parting line indentation, parting line projection, and porosity.

Backrind is a longitudinal recess of a wide angle U-like or W-like cross section located at a mold section parting line. It is caused by thermal expansion over a sharp mold edge or by premature cure. Blisters are voids or holes in the body of the O-ring. Flash is a very thin gage, sometimes film-like, material which extends from parting line projections. Flow marks are recesses caused by incomplete flow of the material forming the O-ring. Foreign materials are any extraneous, embedded matter or depression formed in the surface of the O-ring.

In regard to the other surface defects, mismatch occurs when the cross sectional radius in one ring half is unequal to that of the other ring half. This is caused by a dimensional difference in mold halves. Mold deposit indentations are caused by a build up of hardened deposits adhering to the mold cavity and result in indentations, and rough surface texture of the O-ring. Non-fill results in randomly spaced, irregularly shaped, surface indentations having a course texture. Off-register is misaligned O-ring halves caused by a lateral shift of one mold cavity plate relative to another mold cavity plate. Parting line indentation is a shallow, saucer-like recess located on a parting line and caused by a deformity in the mold edge. Parting line projection is a continuous ridge of material situated on the parting line and caused by worn or excessively rounded mold edges. Finally, porosity is the presence of numerous minute voids or sponginess in the O-ring.

The inspecting of O-rings is difficult and time consuming due to the fact that if the O-rings are to be used in critical situations to provide a desired sealing action, the O-rings must be accurately shaped to the desired dimensions and be free of surface flaws. Thus, an O-ring for critical use may typically have an inside or outside diameter which can vary by as little as 0.005 inches and a thickness which can vary by as little as 0.003 inches. When the obtaining of the desired sealing action requires precision dimensioning of an O-ring, the O-ring must be free of all but the very smallest surface flaws. Thus, a surface imperfection having a width of 0.002 inches can, in some situations, lead to a seal failure.

SUMMARY OF THE PRESENT INVENTION

The present invention provides a new and improved method of inspecting O-rings. The method enables the dimensions of a resiliently deflectable O-ring, which tends to distort under the influence of its own weight, to be determined. In addition, the method enables flaws in the surface of the O-ring to be detected.

In order to accurately measure a flexible O-ring without distorting it, the O-ring is placed on a transparent support member with the central axis of the O-ring in a vertical orientation. Light is directed toward the O-ring and through the support member so that the O-ring casts a shadow. Diametral and/or thickness measurements of the O-ring are determined by detecting the distances between portions of the shadow cast by the O-ring.

The O-ring is inspected for surface flaws by directing light toward a small area on the inside and/or outside surface of the O-ring. The O-ring is then rotated about its central axis. A flaw in the surface of the O-ring will cause a variation in the light reflected from the O-ring as it is rotated. In order to enable the entire surface of the O-ring to be inspected, the O-ring may be rotated about an axis which extends transversely to the central axis of the O-ring and extends tangentially to a circle through the center of the cross section of the O-ring.

Accordingly, it is an object of this invention to provide a new and improved method of inspecting a resiliently deflectable O-ring which tends to distort under the influence of its own weight and wherein various dimensions of the O-ring are determined by detecting the distance between portions of a shadow cast by the O-ring.

Another object of this invention is to provide a new and improved method of inspecting an O-ring and wherein the presence of a flaw in the surface of the O-ring is detected by detecting a variation in the light reflected from the surface of the O-ring.

BRIEF DESCRIPTION OF THE DRAWINGS

The foregoing and other objects and features of the present invention will become more apparent upon a consideration of the following description taken in connection with the accompanying drawings wherein:

FIG. 9 is a fragmentary schematic illustration of the manner in which flaws on the inside surface of an O-ring are detected by using the apparatus of FIG. 7;

FIG. 10 is a schematic illustration of the manner in which flaws on the outside surface of an O-ring are detected by using the apparatus of FIG. 7;

DESCRIPTION OF ONE SPECIFIC PREFERRED EMBODIMENT OF THE INVENTION

General Description

The present invention provides a method for measuring a resiliently deflectable O-ring 10 (FIG. 1) and/or locating flaws in the surface of the O-ring. The O-ring 10 is readily deflected from the circular configuration shown in FIG. 1. Thus, if the O-ring 10 is held by a lower radial segment with a central axis 14 of the O-ring extending horizontally, the O-ring will tend to deflect under the influence of its own weight. Due to the relatively small force required to distort the O-ring 10, the obtaining of an accurate measurement of the inside and/or outside diameter of the O-ring is difficult. The locating of relatively small flaws in the surface of the O-ring 10 is also difficult.

Figure 3:
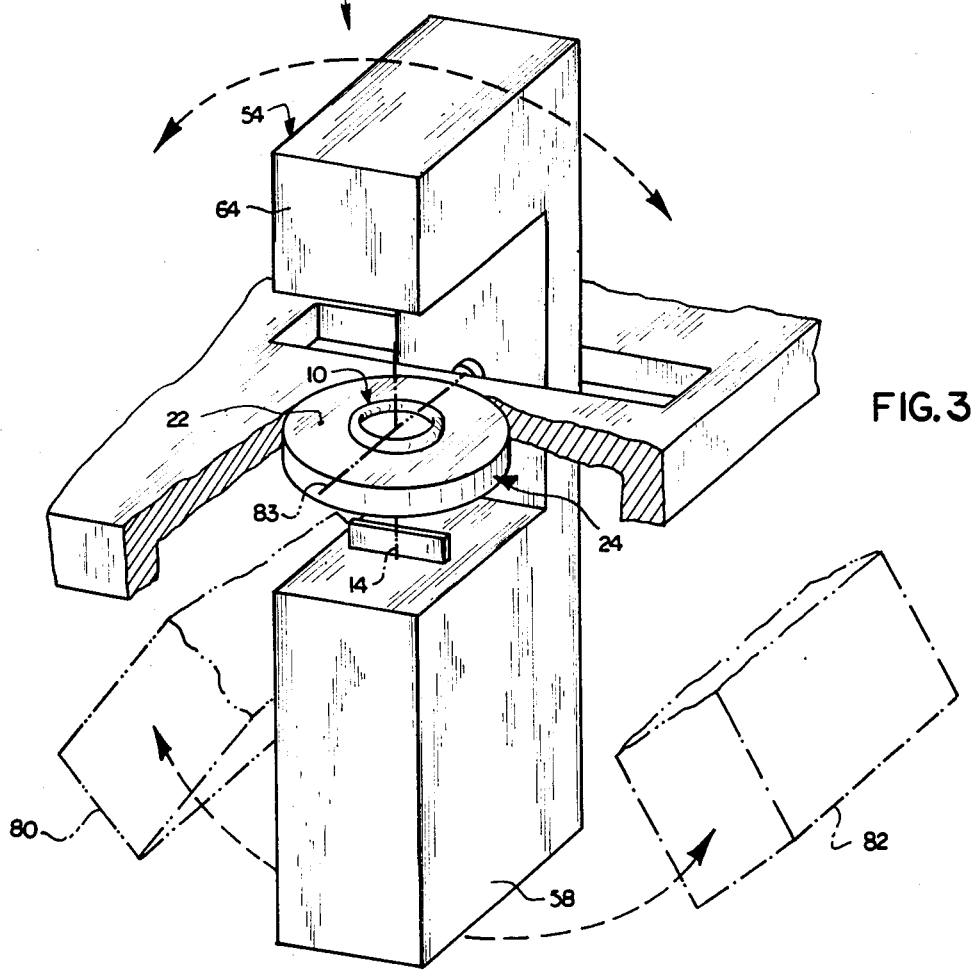
FIG. 3 is a schematic illustration of an apparatus which is operated in accordance with one feature of the present method to determine the dimensions of an O-ring.

In accordance with one of the features of the present invention, an apparatus 18 (see FIG. 3) is operable to accurately measure the O-ring 10. When the O-ring 10 is to be measured, it is placed on a horizontal surface 22 of a rotatable and transparent support member 24. Light is directed through the transparent support member 24 to cause the O-ring to cast a shadow. The inside diameter, outside diameter and/or radial thickness of the O-ring can be measured by detecting the distance between edges of the shadow cast by the O-ring.

In accordance with another of the features of the present invention, an apparatus 28 (see FIG. 7) is used to detect the presence of flaws in the surface of the O-ring 10. The apparatus 28 includes an inside surface inspection station 30 at which an annular inside surface 34 (see FIG. 2) and the radially inward halves of the upper and lower face surfaces 36 and 38 are scanned to detect surface flaws. The apparatus 28 (FIG. 7) includes an outside surface inspection station 32 at which an outside surface 40 (FIG. 2) and the radially outward halves of the upper and lower face surfaces 36 and 38 are scanned to detect surface flaws.

Although an O-ring 10 could have many desired dimensions within a large range of dimensions, it is contemplated that the apparatus 18 and 28 will be used to inspect O-rings having a thickness or radial cross section diameter 44 (FIG. 2) of approximately 0.070 inches. These O-rings will have inside diameters which may vary between 0.614 inches for relatively small O-rings to 5.234 inches for relatively large O-rings. Of course, O-rings having dimensions which are different than these can be inspected with the apparatus 18 and 28.

By using the apparatus 18 to measure the inside and/or outside diameter of the O-ring 10, the diameter can be determined with an accuracy of ±0.0001 inches. This is because the apparatus 18 measures the diameter of the O-ring 10 without contacting the O-ring and while the O-ring is supported on the horizontal surface 22. Therefore, there is almost no tendency for the O-ring to distort at the time when it is being measured.

By using the apparatus 28, it is possible to quickly and easily detect relatively small surface flaws at any location on the surface of an O-ring 10. The surface flaws which are detected by the apparatus 28 may have a width of less than 0.002 inches. It should be understood that the specific O-ring dimensions and accuracy of measurement have been set forth at various places herein for purposes of clarity of illustration and it is not intended that the invention be limited to any specific O-ring dimensions or degree of measurement accuracy.

Measurement of O-Ring

The physical dimensions of the O-ring 10 are measured to determine whether or not its inside diameter, outside diameter, and/or thickness are within specified tolerance ranges. Although the tolerance ranges will vary depending upon the environment in which an O-ring is to be used, it is contemplated that tolerance ranges of ±0.001 of an inch may be specified for O-rings in critical locations. The apparatus 18 (FIGS. 3-5) can be operated to accurately measure the physical dimensions of an O-ring to determine if it is within the specified tolerance ranges.

Figure 4:
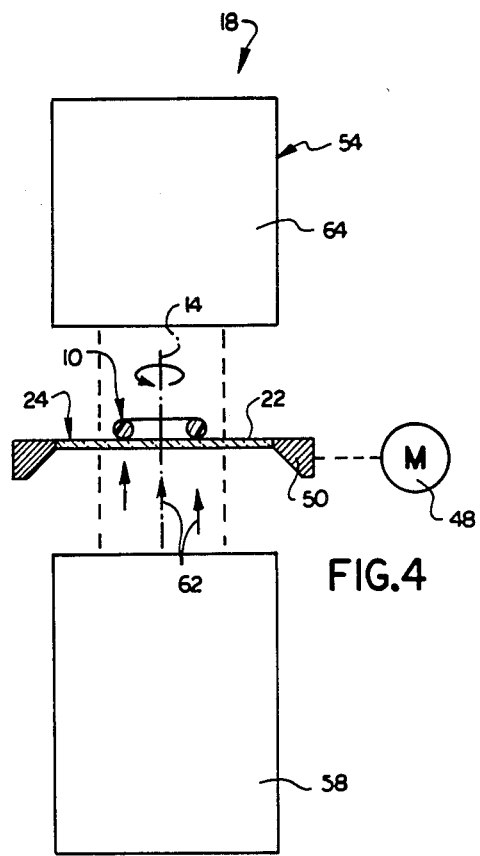
FIG. 4 is an elevational schematic illustration of the apparatus shown in FIG. 3 with a light source and receiver disposed in a vertical orientation relative to an O-ring on a horizontal surface of a transparent support member.

In order to minimize distortion of the O-ring 10 to be measured by the apparatus 18, the O-ring is supported on the flat, horizontal surface 22 of the turntable or support member 24. The turntable 24 is formed of optical glass and is rotatable about its vertical central axis by operation of a motor 48 (FIG. 4). The motor 48 is connected with the table 24 through a suitable gear drive arrangement 50. The O-ring 10 is positioned on the turntable 24 with the central axis 14 of the O-ring extending vertically and coincident with the axis of rotation of the turntable.

A laser shadow gage 54 is operable to measure the O-ring 10 without contacting the O-ring. Thus, the laser shadow gage 54 is operable to scan across a major diameter of the O-ring 10 to provide, in a single reading, an output indicative of the inside diameter, outside diameter and thickness of the O-ring. Since these measurements are made without contacting the O-ring 10 and while the O-ring is supported on the horizontal surface 22, there is very little or no distortion of the O-ring during the measuring. Therefore, accurate measurements can be quickly and easily obtained.

The laser shadow gage 54 includes a transmitter 58 which emits a laser beam, indicated at 62 in FIG. 4, which scans across a major diameter of the O-ring 10 at a very high and uniform speed. The scanning beam appears as a line or plane of light which extends from the transmitter 58 to a receiver 64. The central axis 14 of the O-ring 10 is disposed in the plane swept by the laser beam 62. The receiver 64 collects the light transmitted past the O-ring 10 and converts the light into electronic signals indicative of the distance between edges of a shadow cast by the O-ring. The distance between edges of the O-ring shadow correspond to the inside diameter 68 (FIG. 1), outside diameter 70, and thickness 44 (FIG. 2) of the O-ring 10.

During measurement of the O-ring 10, the light 62 (FIG. 4) from the laser transmitter 58 passes through the transparent turntable 24. A portion of the light is blocked by the O-ring 10 at diametrically spaced apart locations on the O-ring to thereby cast a shadow to the receiver 64. The shadow cast to the receiver 64 has two discrete sections. Each of these sections has a width which is equal to the cross sectional diameter or thickness 44 (see FIG. 2) of the O-ring 10.

Figure 1:
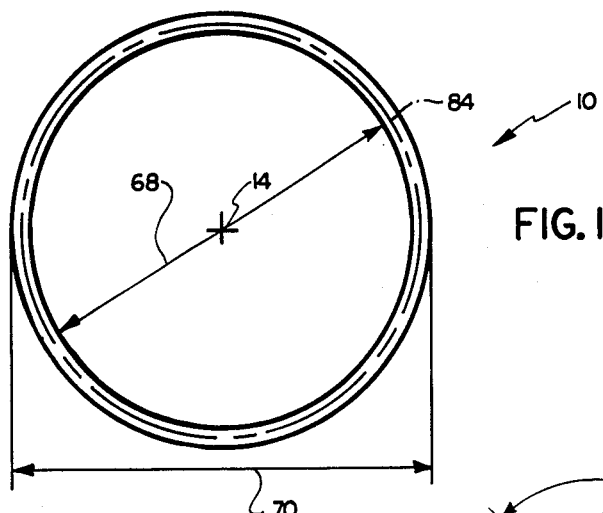
FIG. 1 is a plan view of an O-ring.

The distance between the closest edges of the two shadow sections cast by the O-ring 10 corresponds to the inside diameter, indicated at 68 in FIG. 1, of the O-ring. The distance between the furthest apart edges of the two shadow sections corresponds to the outside diameter, indicated at 70 in FIG. 1, of the O-ring 10. Although the laser transmitter and receiver 58 and 64 (FIG. 3) could have many different constructions, in one specific instance, they were part of a Laser Telemetric System, 1500 series, which is commercially available from Zygo Corporation, Laurel Brook Road, Middlefield, Conn. 06455, U.S.A.

Since the O-ring 10 is supported on the flat, horizontal upper surface 22 of the optically transparent turntable 24 with a central axis 14 of the O-ring extending vertically, there is a minimum of distortion of the O-ring. Therefore, the effect of gravity does not tend to distort the inside and outside diameters 68 and 70 of the O-ring. Gravity effects will tend to compress the thickness or cross sectional diameter 44 of the O-ring. However, the O-ring has a relatively high stiffness of cross sectional thickness and any distortion due to the effects of gravity will be insufficient to affect the measurement readings. If the O-ring 10 was supported in an upright orientation, that is with the central axis 14 extending horizontally, the effect of gravity would distort the inside and outside diameters 68 and 70 of the O-ring.

The O-ring 10 is positioned on the transparent turntable 24 with the central axis 14 of the O-ring extending through the center of rotation of the turntable. Therefore, operation of the motor 48 rotates both the turntable 24 and O-ring 10 about the vertical axis 14 of the O-ring. Stepwise rotation of the turntable 24 enables the laser beam 62 (FIG. 4) to scan diametrically across the O-ring 10 at a plurality of locations. Thus, the laser beam 62 scans across the O-ring 10 along a plane which contains the axis of rotation of the turntable 24 and the coincident axis 14 of the O-ring.

Measuring the inside and/or outside diameter of the O-ring 10 at a plurality of locations enables a noncircular or oval condition of the O-ring to be detected. The plurality of measurements also enable the inside and/or outside diameters of the O-ring to be computed when the O-ring is deflected to a circular configuration upon installation. In addition, rotating the O-ring 10 about its vertical central axis 14 enables the thickness or cross sectional diameter 44 (FIG. 2) to be measured at a plurality of locations on the circumference of the O-ring.

Figure 6:
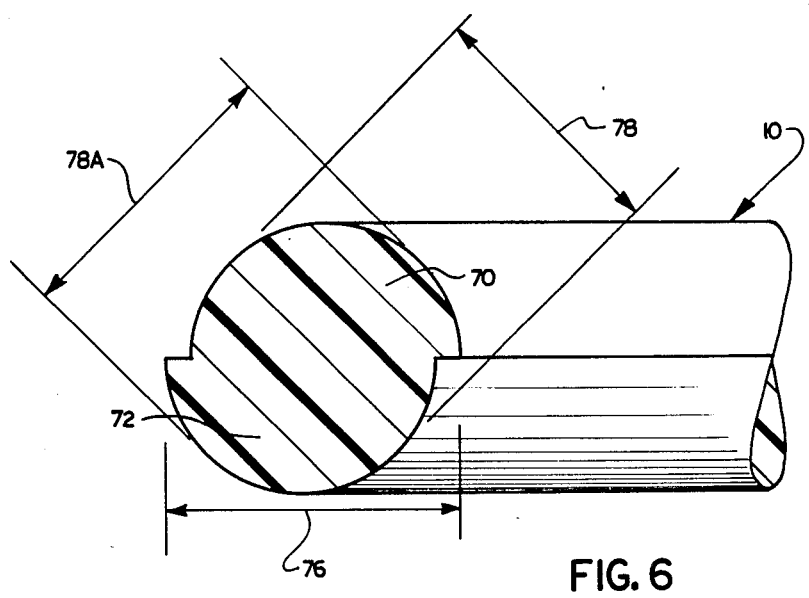
FIG. 6 is a radial sectional view, generally similar to FIG. 2, of an O-ring which is defective due to off-register.

The O-ring 10 may be formed with defects which result in the O-ring having a noncircular cross sectional configuration. Thus, the O-ring 10 could be formed with misaligned O-ring halves 70 and 72 (see FIG. 6). The off-register condition illustrated in FIG. 6 is caused by a lateral shift of one mold cavity plate relative to the other mold cavity plate during casting of the O-ring. Of course, there are other defects which could cause the O-ring 10 to have an uneven cross sectional configuration.

Figure 2:
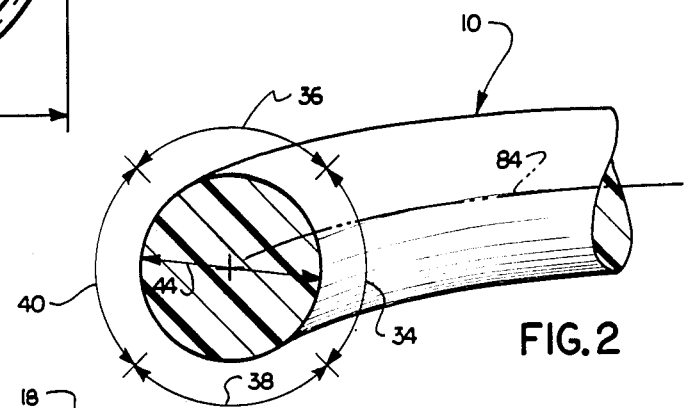
FIG. 2 is a sectional view, on a generally radial plane, illustrating the thickness of and the location of surfaces on the O-ring of FIG. 1.

When an O-ring 10 has a noncircular cross section, in the manner shown in FIG. 6, the uneven cross section could not be detected when the O-ring is scanned from one direction. However, the noncircular condition of the O-ring cross section shown in FIG. 6 can be detected by viewing the O-ring from two or more directions and comparing the apparent cross sectional diameters of the O-ring. If the O-ring has a circular cross section, as shown in FIG. 2, the apparent diameter would be the same for each direction of viewing. If the O-ring has a noncircular cross section, as shown in FIG. 6, the apparent diameter would be different for different viewing directions.

For example, if an O-ring having the noncircular or mismatched condition illustrated in FIG. 6 was viewed from only the vertical direction as illustrated in FIG. 4, the O-ring would cast a shadow and appear to have a thickness corresponding to the dimension indicated at 76 in FIG. 6. By tilting the laser shadow gage 54, the laser beam 62 is directed along an axis which is skewed relative to the central axis 14 of the O-ring 10, in the manner shown in FIG. 5. The shadow of the O-ring at one of the intersection points with the laser beam would then indicate that the O-ring has a cross sectional thickness corresponding to the dimension 78 in FIG. 6. The other intersection of the O-ring with the laser beam would indicate that the O-ring has a cross sectional thickness corresponding to the dimension 78A in FIG. 6. These two dimensions, shown as 78 and 78A, represent the minimum and maximum dimension resulting from the missmatch condition illustrated in FIG. 6. These two dimensions could then be compared with the dimension 76 measured when the laser shadow gage 54 was in the vertical dimension illustrated in FIG. 4. As one can readily see, when the direction 78 is measured at one point on the O-ring, dimension 78A will be measured at the same point on the O-ring after it has been rotated 180° on the turntable 24 without changing the inclination of the laser shadow gage 54. Since the dimension 76 is larger than the dimension 78 and less than the dimension 78A, a comparison of the three dimensions indicates that the cross section has a noncircular configuration.

There are certain defects, such as mismatch, which might conceivably require the O-ring to be viewed from several different angles in order to detect the out of round cross sectional condition of the O-ring. Therefore, the shadow gage 54 is advantageously pivotal in a clockwise direction and in a counterclockwise direction from the upright orientation shown in FIG. 4, to view the cross section of the O-ring from several different vantage points. Thus, when the shadow gage is pivoted in a clockwise direction from the upright orientation shown in FIG. 4, the O-ring is viewed from the vantage point indicated at 80 in FIG. 3 and in FIG. 5. When the shadow gage is pivoted in a counterclockwise direction from the orientation shown in FIG. 4, the O-ring is viewed from the opposite vantage point, indicated at 82 in FIG. 3. In order to enable the O-ring to be viewed from different vantage points, the shadow gage 54 is pivotal about an axis 83 which extends through the plane of the horizontal upper surface 22 of the transparent support table 24.

Detection of Surface Flaws

An O-ring 10 could be formed with many different types of surface flaws. Some of these flaws are backrind, blister, bloom, excessive trimming, flash, flaw marks, foreign material, mismatch, mold deposit indentations, non-fill, off-register, parting line indentation, parting line projection and porosity. Any one of these various surface defects can lead to failure of an O-ring to properly seal. Therefore, when an O-ring is to be used in a critical situation, it must be inspected for these surface flaws.

Figure 8:
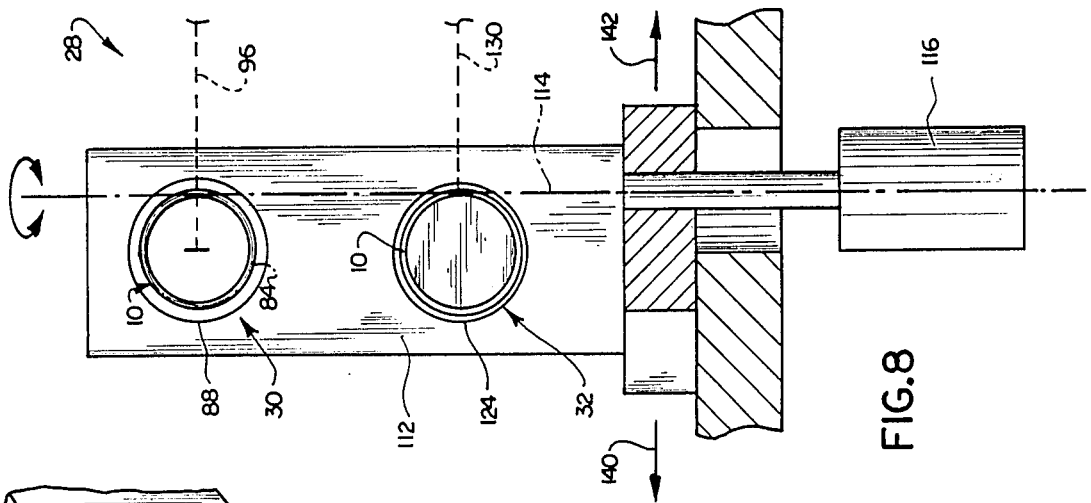
FIG. 8 is an elevational view, taken generally along the line 8—8 of FIG. 7, illustrating the relationship of a pair of O-rings being inspected for surface flaws to a vertical axis about which a fixture for supporting the O-rings is rotated.
Figure 7:
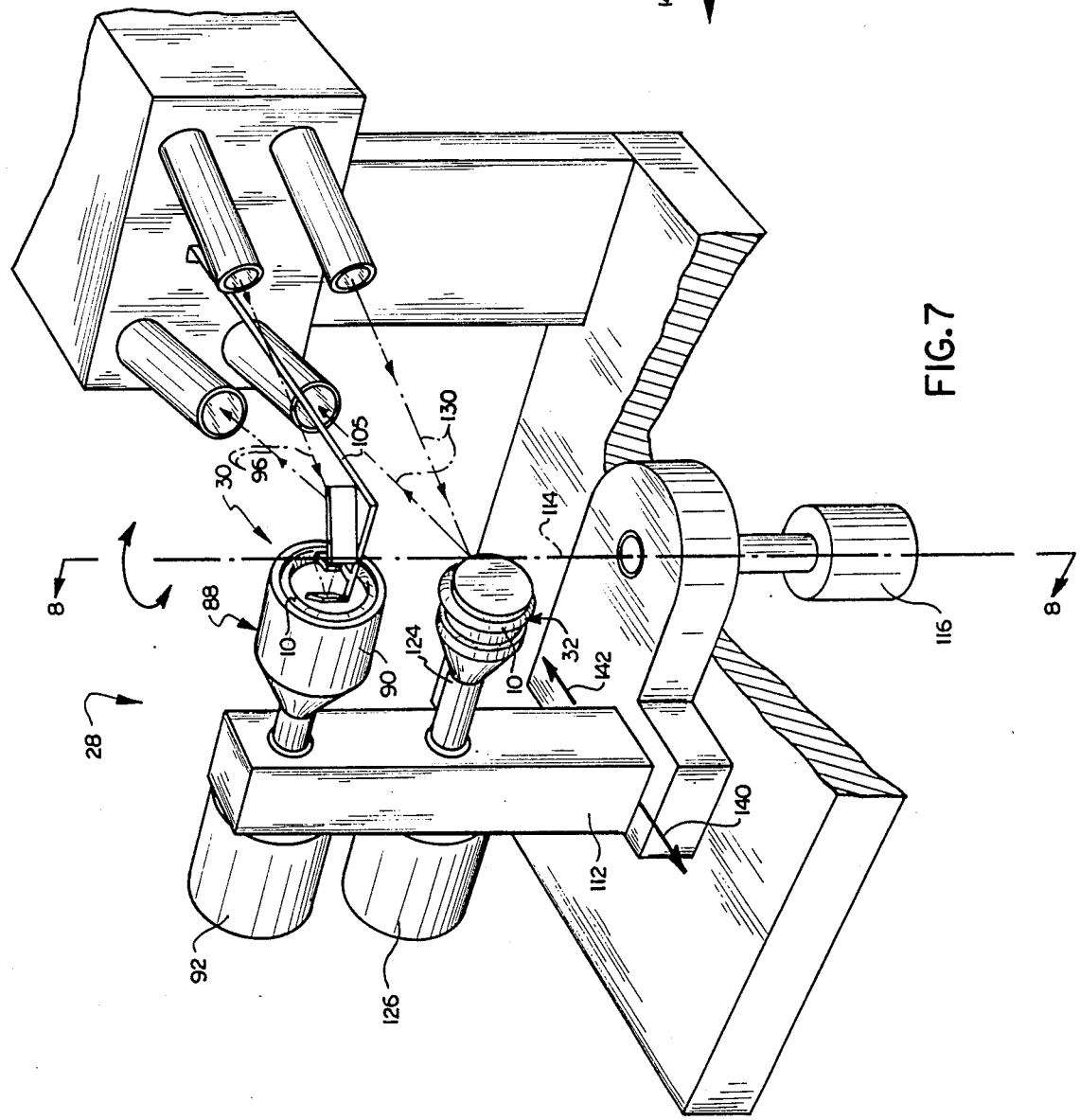
FIG. 7 is a schematic illustration of an apparatus which is operated in accordance with one feature of the present method to locate flaws on inside and outside surfaces of an O-ring.

In order to detect the presence of any possible flaws in the surface of the O-ring 10, the entire surface of the O-ring must be scanned. Thus, the radially inner one-half or 180° of the O-ring surface is scanned at the inside surface inspection station 30 (FIGS. 7 and 8). The radially outer one-half or 180° of the O-ring surface is scanned at the outside surface inspection station 32.

To scan the O-ring surfaces at the inside or outside inspection station 30 or 32, a light beam is directed against a small area on the surface of the O-ring. The O-ring is then rotated about its central axis 14. As the O-ring 10 is rotated through one complete revolution about its central axis 14, the light beam scans a circular path having a width corresponding to the width of the light beam. In order to provide for scanning of the entire inner or outer one-half of the O-ring surface at the inside or outside inspection station 30 or 32, the O-ring 10 is rotated about a point on a circular line 84 (FIGS. 1 and 2) which extends through the center of the circular cross section of the O-ring as the O-ring is rotated about its central axis.

The surface flaw detection apparatus 28 (FIG. 7) includes a spindle 88 which is disposed at the inside surface inspection station 30. The spindle 88 has a cylindrical outer end portion 90 (FIGS. 7 and 9) which circumscribes or extends around the O-ring 10 to support the O-ring. The spindle 88 is rotated about its horizontal central axis by a servo motor 92.

During rotation of the O-ring by the spindle 88, a beam 96 of collimated light from a light source 98 (FIG. 9) is directed against the inside surface 34 of the O-ring 10. Thus, light is collimated to a beam 96 by a suitable lens system 100 and reflected by mirrors 102 and 104 disposed on a horizontal support member 105. The beam 96 of light impinges against the inside surface 34 of the O-ring 10.

The beam of light is reflected from the surface of the O-ring 10 to a mirror 106 (FIG. 9). The mirror 106 directs the reflected light to a portion of the mirror 104. The mirror 104 directs the reflected light back to the mirror 102 and through a lens 107 to a self-scanning photodiode array 108.

The output from the photodiode array 108 varies with variations in the intensity of the light reflected from the surface of the O-ring 10. The presence of any one of the aforementioned defects at the surface of the O-ring 10 will cause a variation in the intensity of the light reflected to the photodiode array 108. The output from the photodiode array 108 is transmitted to a suitable controller. Any variation in the output from the photodiode array 108 indicates the presence of a surface defect on the inside of the O-ring 10.

It is contemplated that the self-scanning photodiode array 108 could have many different constructions. However, in one specific instance, a Reticon G-series self-scanning photodiode array was associated with a Reticon RC-300 series circuit board. This apparatus is commercially available from Reticon Corporation, 910 Benecia Avenue, Sunnyvale, Calif. 94086, U.S.A. In this one specific instance, the light source 98 and lens system 100 included Xeon-mercury lamp associated with a LH 150 lamp housing and lenses from Kratos Analytical Instruments, 170 Williams Drive, Ramsey, N.J. 07446, U.S.A. An LPSA 253 feedback amplifier supplied by Kratos Scoffel Instruments, 24 Booker Street, Westwood, N.J. 07675, U.S.A. was used to stabilize the output from the lamp. Of course, other known photodiode arrays, circuit boards, light sources, lenses and feedback amplifiers could be used if desired.

As the O-ring 10 is rotated about its central axis by the spindle 88, a spot of collimated light, having a diameter of approximately 0.020 inches, is focused on the inside surface 34 of the O-ring. Rotation of the O-ring through one complete revolution results in the collimated light beam 96 scanning a circular path along the inside surface of the O-ring. However, the beam 96 of light has a width sufficient to cover only a portion of the inside surface of the O-ring. Therefore, only an annular strip on the inside surface 34 of the O-ring is scanned for surface flaws by the light beam 96 during one revolution of O-ring 10.

Due to the relatively small size of the area illuminated by the light beam 96, the O-ring must be rotated about a point on the center line 84 (FIGS. 1 and 2) to axially offset the circular path which the beam of light scans on the next succeeding revolution of the O-ring from the previously scanned circular path. To this end, the spindle 88 and motor 92 are supported on a structure 112 (FIGS. 7 and 8) which is rotatable about an axis 114 by operation of a motor 116. The axis 114 extends perpendicular to the central axis 14 of the O-ring and tangentially to the circle 84 which extends through the center of the O-ring cross section (see FIG. 2).

The beam 96 of light is focused on the surface of the O-ring 10 at a point which is disposed radially outwardly from the point of tangency of the axis 114 with the circular line 84 through the center of the O-ring section. Rotation of the O-ring 10 and support structure 112 about the axis 114 results in a change in the small area of the O-ring 10 illuminated by the light beam 96 without changing the spatial relationship between the illuminated area and the lens system 100. If the O-ring has a circular cross sectional configuration throughout its length, the light beam 96 is always focused on the surface of the O-ring 10 during rotation of the O-ring 10 about its central axis 14 and about the axis 114. By rotating the O-ring 10 about the two axes 14 and 114, the entire inner one-half of the surface of the O-ring 10 can be scanned without refocusing the light beam 96.

The inner one-half of the surface of the O-ring 10 is inspected at the inside surface inspection station 30. Thus, the support structure 112 is pivoted about the axis 114 through a distance sufficient to cause the light beam 96 to scan the surface area of the O-ring disposed on the inside of a cylindrical plane extending through the circle 84 and coaxial with the central axis 14 of the O-ring. It is preferred to slowly index the support structure 112 about the axis 114 as the spindle 88 is rotated about its central axis. This causes the light beam 96 to sweep a continuous helical path around the inside surface of the O-ring. The speed of rotation of the structure 112 about the axis 114 is such that successive turns of the helical path which is scanned by the light beam 96 overlap to be certain that any defect on the inside surface of the O-ring is detected.

Surface flaws in the outer one-half of the O-ring 10 are detected at the outside surface inspection station 32 (FIG. 7). The O-ring 10 is mounted on a fixture 124 which is rotated by a motor 126 about an axis which is coincident with a horizontal central axis 14 of the O-ring. A beam 130 (FIG. 10) of collimated light from a light source 132 is directed against the outer side surface of the O-ring 10. The light is collimated by a known lens arrangement 134. The light reflected from the outer side surface of the O-ring 10 is directed back through a lens system 137 to a self-scanning photodiode array 138.

As the O-ring 10 is rotated about its horizontal central axis 14, the beam 130 of light scans the outer surface of the O-ring 10 along a circular path. If the beam of light encounters any surface flaws as it scans the outer side surface of the O-ring 10, the intensity of the light directed back to the self-scanning photodiode array 138 will vary. This variation in intensity results in variation in an output signal transmitted from the diode array 138 to a controller to indicate the presence of a flaw on the surface of the O-ring 10.

The beam of light 130 forms a spot on the outer side surface of the O-ring. This spot has a diameter of approximately 0.020 inches which is less than the width or thickness of the O-ring 10. Therefore, in order to detect a surface defect anywhere on the outer one-half of the surface of the O-ring, the beam of light 130 must scan the O-ring at a plurality of locations. To provide for the scanning of the O-ring at a plurality of locations, the O-ring 10 is rotated about the vertical axis 114 which extends tangentially to the circle 84 through the center of the cross section of the O-ring (see FIGS. 1 and 2). The light beam 130 is focused on the surface of the O-ring at a location which is radially outwardly from the point at which the axis 114 intersects the center line circle 84 of the O-ring cross section.

In order to provide scanning of the entire outer one-half of the surface of the O-ring 10, the O-ring is rotated slowly about the vertical axis 114 as it is slowly rotated about its own horizontal central axis 14. The rate of rotation of the O-ring 10 about the axis 114 is such that on each revolution of the O-ring 10, the light beam 130 is shifted by a distance which is slightly less than the diameter of the spot at which the beam of light impinges on the outer side surface of the O-ring 10. Therefore the entire outer one-half of the surface of the O-ring 10 is scanned by the light beam 130.

Since the mounting fixtures 88 and 124 at the inside and outside inspection stations are connected with the support structure 112 (see FIG. 7) for rotation about a common axis 114, the same motor 116 can be used to rotate two O-rings about the axis 114 while they are simultaneously inspected. In order to enable the inside and outside surfaces of O-rings of somewhat different diameters to be simultaneously inspected, it is contemplated that the fixtures 88 and 124 will be mounted for movement toward and away from the vertical axis 114 in the manner illustrated by the arrows 140 and 142 in FIGS. 7 and 8. Of course, if desired, only the inside surface of a plurality of O-rings could be simultaneously inspected at one location and only the outside surfaces of a plurality of O-rings could be simultaneously inspected at another location.

Control Apparatus

Figure 11:
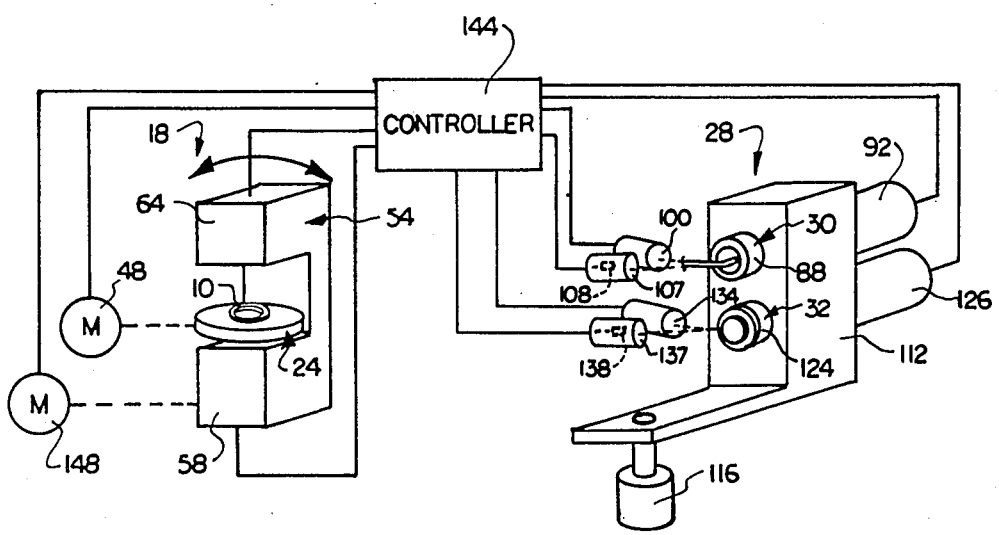
FIG. 11 is a schematic illustration of controls associated with the apparatus shown in FIGS. 3 and 7.

A controller 144 is provided to control the operation of the measuring apparatus 18 and surface flaw detection apparatus 28 (see FIG. 11). The controller 144 is connected with the laser transmitter 58 to initiate transmittal of a beam through the transparent O-ring support table 24. An output signal from the receiver 64 then indicates the dimensional characteristics of a shadow cast by the O-ring 10. The output from the receiver 64 is transmitted to the controller 144. When the dimensional characteristics of an O-ring 10 have been determined at a first location, the controller 144 energizes the motor 48 to rotate the turntable 24 through less than a full revolution so that the dimensional characteristics of the O-ring can be determined at another location.

Figure 5:
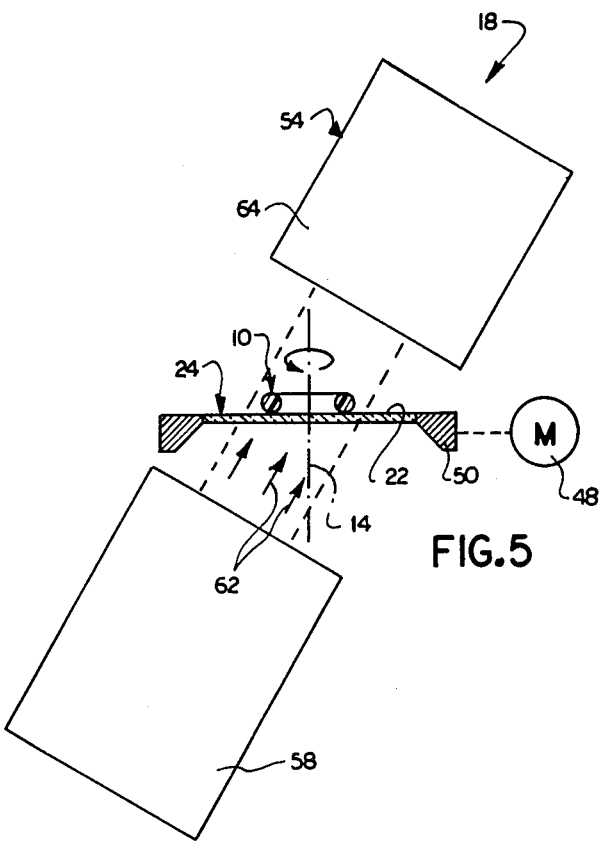
FIG. 5 is a schematic illustration, generally similar to FIG. 4, with the light source and receiver in a tilted relationship relative to the O-ring and transparent support member.

Once the dimensional characteristic of an O-ring have been determined with the laser shadow gage 54 in the upright orientation of FIG. 4, a motor 148 energized by the controller 144 to tilt the laser shadow gage to an orientation in which it is skewed relative to the central axis of the O-ring, in the manner illustrated in FIG. 5. The dimensional characteristics of the O-ring 10 are then determined at a plurality of locations by rotating the O-ring about the horizontal support table 24 with the shadow gage 54 tilted. This enables an out-of-round cross sectional configuration of the O-ring at any one of a plurality of locations to be detected.

In addition to controlling the operation of the dimensional inspection apparatus 18, the controller 144 controls the operation of the surface flaw detection apparatus 28. Thus, the controller 144 effects energization of the light sources 98 and 132 (see FIGS. 9 and 10) to direct light against the inner and outer side surfaces of the O-rings 10 on the fixtures 88 and 124. Signals corresponding to the intensity of the light reflected from the surface of the O-ring are transmitted to the controller from the self-scanning photodiode arrays 108 and 138.

As the fixtures 88 and 124 are rotated about horizontal central axes, the controller 144 effects operation of the motor 116 to slowly rotate the fixture 112 about the vertical axis 114 (FIG. 7). The light beams 96 and 130 (FIGS. 9 and 10) directed against the O-rings 10 on the fixtures 88 and 124 scan the surface of the O-rings in a continuous helical path having overlapping turns. Therefore, surface defects anywhere on the inner and outer side surfaces of the O-rings 10 are detected.

The controller 144 is connected with a printer (not shown) which provides a record of the dimensional characteristics of an O-ring 10 being measured in the apparatus 18 and the presence of surface flaws on the O-rings being inspected by the apparatus 28. In addition, the controller 144 computes the deviations of the measured dimensions from required dimensions, shows individual piece variance from the required dimensions, and provides a statistical evaluation of this data. When the presence of a flaw is detected on the surface of an O-ring, the output of the controller 144 indicates the size of the flaw and which of various levels of acceptance and rejection was met by an O-ring.

It is contemplated that automatic loading equipment could be used to position O-rings on the transparent turntable 24 and the fixtures 88 and 124 if desired. Although it is preferred to detect the presence of flaws on the surface of an O-ring by detecting variations in the intensity of the light reflected from the surface of the O-ring, it is contemplated that variations in other characteristics of the light as a result of encountering a flaw could be detected if desired.

O-Ring Positioning Apparatus

It is contemplated that an O-ring 10 could be positioned on the turntable 24 manually or with many different types of positioning devices. In one specific instance, a positioning apparatus 154 (see FIG. 12) was used to move an inspected O-ring 10a off of the turntable 24 and to move a next succeeding O-ring 10b onto the turntable 24. The positioning apparatus 154 includes a positioning member 156 having a leading end portion 158 which is arcuately recessed to engage an inspected O-ring 10a on the turntable 24. A circular opening 160 in the positioning member 156 engages a next succeeding O-ring 10b.

Figure 12:
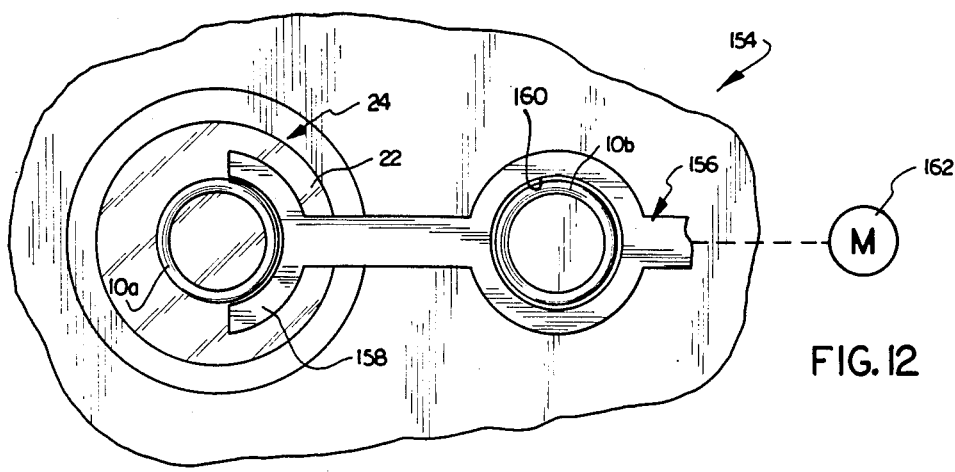
FIG. 12 is a schematic illustration of a positioning member engaging an inspected O-ring on a turntable of the apparatus of FIG. 3 and the next succeeding O-ring to be moved to the inspection station.

The positioning member 156 is driven by a motor 162 through a suitable drive mechanism (not shown) to move the positioning member leftwardly from the position shown in FIG. 12. As the positioning member 156 moves leftwardly from the position shown in FIG. 12, the leading end portion 158 of the positioning member pushes the inspected O-ring 10a off of the turntable 24. At the same time, the cylindrical inside surface of the opening 160 pushes the next succeeding O-ring 10b onto the turntable 24. The positioning member 156 is moved through a longitudinal distance sufficient to locate the O-ring 10b on the turntable 24 with the central axis of the O-ring coincident with the central axis 14 of the turntable (see FIG. 13).

Figure 13:
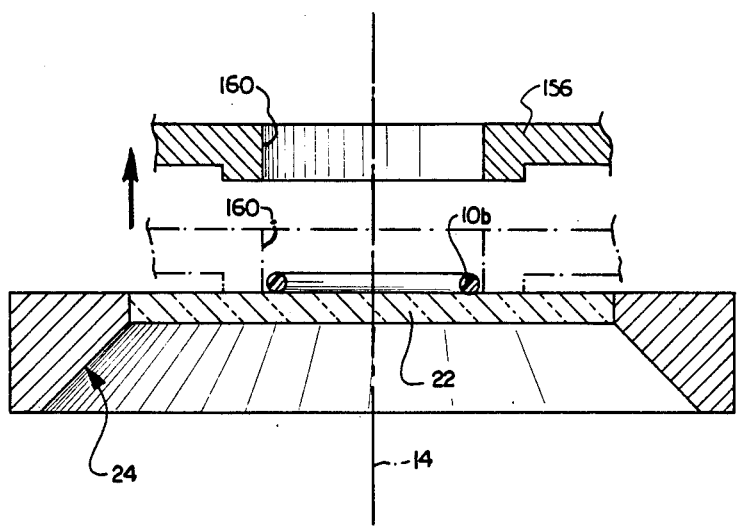
FIG. 13 is a schematic illustration of the manner in which an O-ring is moved to the inspection station by the positioning member of FIG. 12 and the manner in which the positioning member is raised before being moved back to engage a next succeeding O-ring.

Once an inspected O-ring 10a has been moved off the turntable and a next succeeding O-ring 10b positioned on the turntable, the positioning member 156 is raised upwardly to clear the O-ring in the manner shown schematically in FIG. 13. The positioning member is then moved rightwardly (as viewed in FIG. 13) to a position in which the leading end portion 158 of the positioning member 156 is clear of the turntable 22. The next succeeding O-ring (not shown) is then engaged in the circular opening 160 of the positioning member 156. Once the O-ring 10b has been inspected, the positioning member 156 is moved toward the left (as viewed in FIGS. 12 and 13) to push the inspected O-ring 10b off of the turntable 22 and move the next succeeding O-ring (not shown) onto the turntable.

Conclusion

The present invention provides a new and improved method of inspecting O-rings 10. The method enables the dimensions of a resiliently deflectable O-ring 10, which tends to distort under the influence of its own weight, to be determined without contacting the O-ring. In addition, the method enables flaws at the surface of the O-ring to be detected.

In order to accurately measure a flexible O-ring 10 without distorting it, the O-ring is placed on a transparent support member 24 with the central axis 14 of the O-ring in a vertical orientation. Light is directed toward the O-ring 10 and through the support member 24 so that the O-ring casts a shadow. Diametral and/or thickness measurements of the O-ring 10 are determined by detecting the distances between portions of the shadow cast by the O-ring.

The O-ring 10 is inspected for surface flaws by directing light toward a small area on the inside and/or outside surface of the O-ring 10. The O-ring is then rotated about its central axis. Any surface flaws in the surface of the O-ring 10 will cause a variation in the light reflected from the O-ring as it is rotated. In order to enable the entire surface of the O-ring 10 to be scanned, the O-ring is rotated about an axis 114 which extends transversely to the central axis 14 of the O-ring 10 and extends tangentially to a circle 84 through the center of the cross section of the O-ring.

Having described one specific preferred embodiment of the invention, the following is claimed:

1. A method for inspecting a resiliently deflectable O-ring which tends to distort under the influence of its own weight when supported at one segment with its central axis extending horizontally, said method comprising the steps of providing a transparent support member, placing an O-ring on the transparent support member with the central axis of the O-ring in a vertical orientation, directing light toward the O-ring and through the transparent support member to cause the O-ring to cast a shadow, said step of directing light toward the O-ring includes the step of scanning the O-ring with a narrow beam of light along a path which extends through the center of the O-ring, and detecting the distance between portions of the shadow cast by the O-ring to determine a diametral measurement of the O-ring, said step of detecting the distance between portions of the shadow cast by portions of the O-ring includes detecting the distance between portions of a shadow cast by scanning the O-ring with the narrow beam of light with the O-ring in a first position, said method further including the steps of rotating the transparent support member about a vertical axis which extends through the center of the O-ring to move the O-ring to a second position, scanning the O-ring with a narrow beam of light along a path which extends through the center of the O-ring when the O-ring is in the second position, and detecting the distance between portions of a shadow cast by scanning the O-ring with the narrow beam of light with the O-ring in the second position.

2. A method as set forth in claim 1 wherein said step of placing the O-ring on the transparent support member includes the step of pushing the O-ring onto the support member with a positioning member.

3. A method of inspecting a resiliently deflectable O-ring which tends to distort under the influence of its own weight when supported at one segment with its central axis extending horizontally, said method comprising the steps of providing a transparent support member, placing an O-ring on the transparent support member with the central axis of the O-ring in a vertical orientation, directing light toward the O-ring and through the transparent support member to cause the O-ring to cast a shadow, said step of directing light toward the O-ring includes directing light toward the O-ring along a path having a longitudinal axis with a first angular orientation relative to the central axis of the O-ring, and detecting the distance between portions of the shadow cast by the O-ring to determine a diametral measurement of the O-ring, said method further including the steps of detecting the distance between edge portions of a shadow cast by a portion of the O-ring disposed in one radial plane while directing light along the path having the first angular orientation relative to the O-ring to determine a first thickness measurement of the O-ring at a first location along the circumference of the O-ring, directing light toward the O-ring along a path having a longitudinal axis with a second anular orientation relative to the central axis of the O-ring, and detecting the distance between edge portions of the shadow cast by the portion of the O-ring in the one radial plane while directing light along the path having the second angular orientation relative to the O-ring to determine a second thickness measurement of the O-ring at the first location along the circumference of the O-ring.

4. A method of inspecting a resiliently deflectable O-ring which tends to distort under the influence of its own weight when supported at one segment with its cental axis extending horizontally, said method comprising the steps of providing a transparent support member, placing an O-ring on the transparent support member with the central axis of the O-ring in a vertical orientation, directing light toward the O-ring and through the transparent support member to cause the O-ring to cast a shadow, detecting the distance between portions of the shadow cast by the O-ring to determine a diametral measurement of the O-ring, directing light against at least a portion of the outside surface area of the O-ring, and detecting variations in the light reflected from the outside surface area of the O-ring to thereby detect the presence of surface flaws in at least a portion of the outside surface area of the O-ring.

5. A method as set forth in claim 4 further including the step of rotating the O-ring about its central axis while performing said step of directing light against at least a portion of the outside surface area of the O-ring, said step of detecting variations in the light reflected from the outside surface area of the O-ring being performed during rotation of the O-ring to detect the presence of flaws throughout the circumferential extent of at least a portion of the outside surface area of the O-ring.

6. A method as set forth in claim 5 further including the step of rotating the O-ring about an axis which extends transversely to the central axis of the O-ring, said method further including the step of directing light against at least a portion of the inside surface area of the O-ring while rotating the O-ring about its central axis, and detecting variations in the light reflected from the inside surface area of the O-ring to thereby detect the presence of flaws in the inside surface area of the O-ring.

7. A method of inspecting a resiliently deflectable O-ring which tends to distort under the influence of its own weight when supported at one segment with its central axis extending horizontally, said method comprising the steps of providing a transparent support member, placing an O-ring on the transparent support member with the central axis of the O-ring in a vertical orientation, directing light toward the O-ring and through the transparent support member to cause the O-ring to cast a shadow, detecting the distance between portions of the shadow cast by the O-ring to determine a diametral measurement of the O-ring, directing light against at least a portion of the inside surface area of the O-ring, and detecting variations in the light reflected from the inside surface area of the O-ring to thereby detect the presence of surface flaws in at least a portion of the inside surface area of the O-ring.

8. A method of inspecting a resiliently deflectable O-ring which tends to distort under the influence of its own weight when supported at one segment with its central axis extending horizontally, said method comprising the steps of providing a transparent support member, placing an O-ring on the transparent support member, scanning the O-ring with a narrow beam of light along a first path which extends through the center of the O-ring to cause the O-ring to cast a first shadow having two separate sections formed by diametrically spaced apart first portions of the O-ring, detecting the distance between the two sections of the first shadow cast by the O-ring to determine a first diametral measurement of the O-ring, scanning the O-ring with a narrow beam of light along a second path which extends through the center of the O-ring in a direction transverse to the first path to cause the O-ring to cast a second shadow having two separate sections formed by diametrically spaced apart second portions of the O-ring which are spaced from the first portions of the O-ring, and detecting the distance between the two sections of the second shadow cast by the O-ring to determine a second diametral measurement of the O-ring.

9. A method as set forth in claim 8 further including the step of directing light against at least a portion of the outside surface area of the O-ring, and detecting variations in the light reflected from the outside surface area of the O-ring to thereby detect the presence of surface flaws in at least a portion of the outside surface area of the O-ring.

10. A method as set forth in claim 8 further including the step of directing light against at least a portion of the inside surface area of the O-ring, and detecting variations in the light reflected from the inside surface area of the O-ring to thereby detect the presence of surface flaws in at least a portion of the inside surface area of the O-ring.

11. A method as set forthin claim 8 further including the step of rotating the O-ring about its central axis after performing said step of scanning the O-ring along a first path and prior to performance of said step of scanning the O-ring along a second path.

12. A method for inspecting a resiliently deflectable O-ring which tends to distort under the influence of its own weight when supported at one segment with its central axis extending horizontally, said method comprising the steps of providing a transparent support member, placing an O-ring on the transparent support member, scanning a first section of the O-ring with a narrow beam of light along a first path which extends through the center of the O-ring to cause the O-ring to cast a first shadow having two separate sections formed by first diametrically spaced apart portions of the O-ring, rotating the O-ring about its central axis, thereafter, scanning a second section of the O-ring with a narrow beam of light along a second path which extends through the center of the O-ring and is skewed relative to the first path to cause the O-ring to cast a second shadow having two separate sections formed by second diametrically spaced apart portions of the O-ring, and detecting distances between portions of the first and second shadows cast by the O-ring to determine measurement of the O-ring.

13. A method for inspecting a resiliently deflectable O-ring which tends to distort under the influence of its own weight when supported at one segment with its central axis extending horizontally, said method comprising the steps of:

providing a transparent support member;

placing the O-ring on the transparent support member with its central axis in a vertical orientation;

scanning the O-ring with a narrow beam of light along a path which extends through the center of the ring, including the step of imparting relative movement between the transparent support and the light source;

detecting the distance between portions of the O-ring by measuring the shadows cast by the scanning light;

scanning at least two different portions of the O-ring by moving said O-ring relative to the light source thereby casting at least two different shadows and comparing the dimensions of the different cast shadows.

14. A method of inspecting an O-ring, said method comprising the steps of directing light toward a small area on the inside surface of the O-ring, scanning a first circular portion of the inside surface of the O-ring by rotating the O-ring about its central axis while performing said step of directing light toward the inside surface of the O-ring, detecting variations in the light reflected from the first circular portion of the inside surface of the O-ring to thereby detect the presence of flaws, rotating the O-ring about an axis which extends transversely to the central axis of the O-ring and which extends tangentially to a circle through the center of the cross section of the O-ring, scanning a second circular portion of the inside surface of the O-ring by rotating the O-ring about its central axis while performing said step of directing light toward the inside surface of the O-ring after having performed said step of rotating the O-ring about an axis which extends transversely to the central axis of the O-ring, and detecting variations in the light reflected from the second circular portion of the inside surface of the O-ring to thereby detect the presence of flaws.

15. A method as set forth in claim 14 wherein said step of rotating the O-ring about an axis which extends transversely to the central axis is performed simultaneously with performance of said steps of rotating the O-ring about its central axis and directing light toward a portion of the inside surface of the O-ring.

16. A method as set forth in claim 14 wherein said step of rotating the O-ring about an axis which extends transversely to the central axis of the O-ring includes moving the O-ring through an arcuate distance about the transverse axis sufficient to enable the light to be directed toward a portion of the face surface disposed on a first side of the O-ring and to be subsequently directed toward a portion of the face surface disposed on a second side of the O-ring.

17. A method as set forth in claim 14 further including the step of directing light toward a small area on the outside surface of the O-ring, scanning a first circular portion of the outside surface of the O-ring by rotating the O-ring about its central axis while performing said step of directing light toward the outside surface of the O-ring, and detecting variations in the light reflected from the first circular portion of the outside surface of the O-ring to thereby detect the presence of flaws.

18. A method as set forth in claim 17 further including the step of scanning a second circular portion of the outside surface of the O-ring by rotating the O-ring about its central axis while performing said step of directing light toward the outside surface of the O-ring after having performed said step of rotating the O-ring about an axis which extends transversely to the central axis of the O-ring.

19. A method as set forth in claim 14 further including the steps of providing a transparent support member, placing the O-ring on the transparent support member with the central axis of the O-ring in a vertical orientation, directing light toward the O-ring and through the transparent support member to cause the O-ring to cast a shadow, and detecting the distance between portions of the shadow cast by the O-ring to determine a diametral measurement of the O-ring.

20. A method of inspecting an O-ring, said method comprising the steps of directing light toward a small area on the outside surface of the O-ring, scanning a first circular portion of the outside surface of the O-ring by rotating the O-ring about its central axis while performing said step of directing light toward the outside surface of the O-ring, detecting variations in the light reflected from the first circular portion of the outside surface of the O-ring to thereby detect the presence of flaws, rotating the O-ring about an axis which extends transversely to the central axis of the O-ring and which extends tangentially to a circle through the center of the cross section of the O-ring, scanning a second circular portion of the outside surface of the O-ring by rotating the O-ring about its central axis while performing said step of directing light toward the outside surface of the O-ring after having performed said step of rotating the O-ring about an axis which extends transversely to the central axis of the O-ring, and detecting variations in the light reflected from the second circular portion of the outside surface of the O-ring to thereby detect the presence of flaws.

21. A method as set forth in claim 19 wherein said step of rotating the O-ring about an axis which extends transversely to the central axis is performed simultaneously with performance of said steps of rotating the O-ring about its central axis and directing light toward a portion of the outside surface of the O-ring.

22. A method as set forth in claim 10 further including the steps of providing a transparent support member, placing the O-ring on the transparent support member with the central axis of the O-ring in a vertical orientation, directing light toward the O-ring and through the transparent support member to cause the O-ring to cast a shadow, and detecting the distance between portions of the shadow cast by the O-ring to determine a diametral measurment of the O-ring.

23. A method as set forth in claim 20 wherein said step of rotating the O-ring about an axis which extends transversely to the central axis of the O-ring includes moving the O-ring through an arcuate distance about the transverse axis sufficiently to enable the light to be directed toward a portion of the face surface disposed on a first side of the O-ring and to be subsequently directed toward a portion of the face surface disposed on a second side of the O-ring.

24. A method of inspecting a resiliently deflectable O-ring which tends to distort under the influence of its own weight, said method comprising the steps of directing light toward the O-ring to cause the O-ring to cast a shadow, detecting the distance between portions of the shadow cast by diametrically spaced apart portions of the O-ring to determine a diametral measurement of the O-ring, detecting the distance between portions of the shadow cast by a portion of the O-ring disposed in one radial plane to determine a thickness measurement of the O-ring, directing light toward a small area on the inside surface of the O-ring, rotating the O-ring about its central axis while performing said step of directing light toward the inside surface of the O-ring, detecting variations in the light reflected from the inside surface of the O-ring to thereby detect the presence of flaws, directing light toward a small area on the outside surface of the O-ring, rotating the O-ring about its central axis while performing said step of directing light toward the outside surface of the O-ring, detecting variations in the light reflected from the outside surface of the O-ring to thereby detect the presence of flaws.

25. A method as set forth in claim 24 further including the steps of placing the O-ring on a transparent suppport member, said step of directing light toward the O-ring to cause the O-ring to cast a shadow including the step of directing light through the transparent support member.

26. A method as set forth in claim 24 wherein said step of directing light toward the O-ring to cause the O-ring to cast a shadow includes directing light toward the O-ring along a path having a longitudinal axis with a first angular orientation relative to the central axis of the O-ring, said step of detecting the distance between portions of the shadows past by a portion of the O-ring disposed in one radial plane being performed while performing said step of directing light toward the O-ring along a path having a first angular orientation relative to the central axis of the O-ring, said method further including the steps of directing light toward the O-ring along a path having a longitudinal axis with a second angular orientation relative to the central axis of the O-ring, and detecting the distance between edge portions of a shadow cast by the portion of the O-ring in the one radial plane while directing light along the path having the second angular orientation relative to the O-ring to determine a second thickness measurement of the O-ring at the first location along the circumference of the O-ring.

27. A method as set forth in claim 24 further including the step of rotating the O-ring about an axis which extends transversely to the central axis of the O-ring and which extends tangentially to a circle through the center of the cross section of the O-ring while performing said step of directing light toward a small surface area on the inside surface of the O-ring.

28. A method as set forth in claim 24 further including the step of rotating the O-ring about an axis which extends transversey to the central axis of the O-ring and which extends through the center of the cross section of the O-ring while performing said step of directing light toward a small surface area on the outside surface area of the O-ring.

* * * * *